(12) United States Patent
Kushnir et al.

(10) Patent No.: US 6,685,731 B2
(45) Date of Patent: Feb. 3, 2004

(54) METHOD AND SYSTEM FOR IMPROVING CARDIOVASCULAR PARAMETERS OF A PATIENT

(75) Inventors: Igal Kushnir, Pardes Hana (IL); Nachum Nesher, Zichron Yaakov (IL)

(73) Assignee: M.T.R.E. Advanced Technologies Ltd., Akiva (IL)

( * ) Notice: Subject to any disclaimer, the term of this patent is extended or adjusted under 35 U.S.C. 154(b) by 77 days.

(21) Appl. No.: 09/885,861

(22) Filed: Jun. 20, 2001

(65) Prior Publication Data

US 2002/0032473 A1 Mar. 14, 2002

Related U.S. Application Data

(63) Continuation of application No. PCT/IL00/00554, filed on Sep. 10, 2000.

(30) Foreign Application Priority Data

Sep. 9, 1999 (IL) ................................................ 131834

(51) Int. Cl.[7] .................................................. A61F 7/00
(52) U.S. Cl. ...................................... 607/104; 607/108
(58) Field of Search ........................... 607/96, 104, 108, 607/112

(56) References Cited

U.S. PATENT DOCUMENTS

| | | | | |
|---|---|---|---|---|
| 3,425,486 A | * | 2/1969 | Burton et al. ................. | 165/46 |
| 4,691,762 A | * | 9/1987 | Elkins et al. .................. | 165/46 |
| 4,718,429 A | * | 1/1988 | Smidt .......................... | 607/104 |
| 4,998,415 A | * | 3/1991 | Larsen ......................... | 62/231 |
| 5,269,369 A | * | 12/1993 | Faghri ................... | 165/104.14 |
| 5,443,488 A | | 8/1995 | Namenye et al. ........... | 607/104 |
| 5,755,275 A | | 5/1998 | Rose et al. .................... | 165/46 |
| 5,824,025 A | | 10/1998 | Augustine ................... | 607/107 |
| 5,871,526 A | * | 2/1999 | Gibbs et al. .................. | 165/46 |
| 5,891,187 A | * | 4/1999 | Winthrop et al. ........... | 126/204 |
| 5,967,225 A | * | 10/1999 | Jenkins .................. | 165/104.14 |
| 6,012,179 A | * | 1/2000 | Garrett et al. ................ | 2/456 |
| 6,109,338 A | * | 8/2000 | Butzer ......................... | 165/46 |
| 6,375,673 B1 | * | 4/2002 | Clifton et al. .............. | 607/104 |

FOREIGN PATENT DOCUMENTS

| | | |
|---|---|---|
| WO | 9923980 | 5/1999 |
| WO | 9944552 | 9/1999 |

* cited by examiner

*Primary Examiner*—Roy D. Gibson
(74) *Attorney, Agent, or Firm*—Ladas & Parry

(57) ABSTRACT

Cardiovascular parameters of a patient undergoing a procedure involving general anesthesia are maintained by controlling the patient's body temperature. Such control involves the use of a garment enveloping substantial portions of the patient's body and utilizing a heating/cooling regime taking into consideration the heat transfer dynamics of the body.

6 Claims, 12 Drawing Sheets

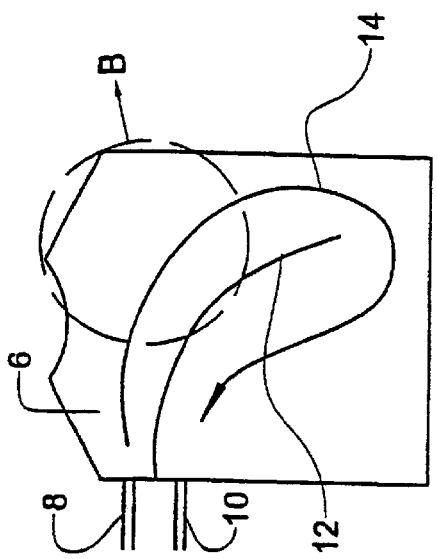
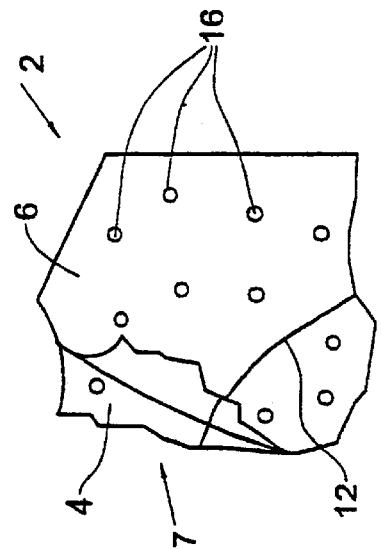
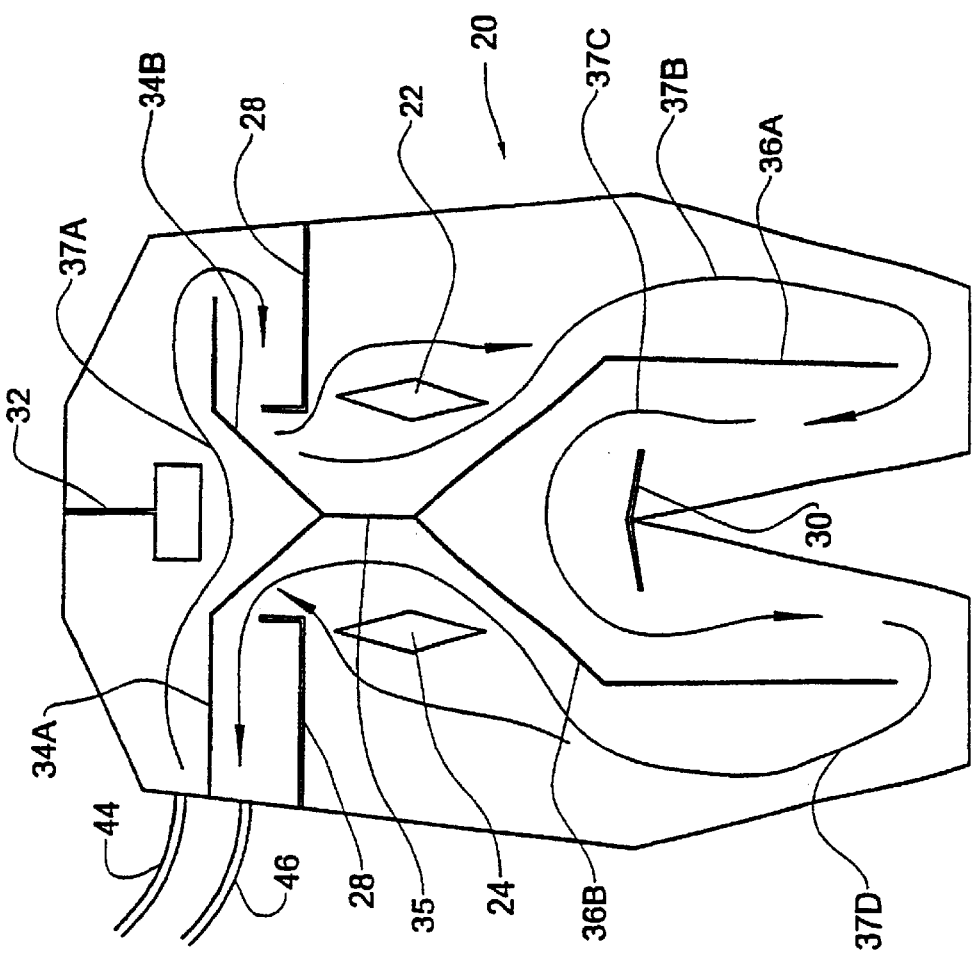

METHOD AND SYSTEM FOR IMPROVING CARDIOVASCULAR PARAMETERS OF A PATIENT

This application is a continuation of PCT/IL00/00554 filed Sep. 10, 2000.

FIELD OF THE INVENTION

The present invention relates to methods and systems for improving cardiovascular parameters and cardiac markers of patients undergoing medical procedures involving general anesthesia. In particular, the present invention relates to methods and systems for improving cardiovascular parameters, in particular cardiac index (CI), systemic vascular resistance (SVR), and the circulating level of the cardiac protein Troponin I (cTnI) of patients during or after open heart surgery.

BACKGROUND OF THE INVENTION

There are many surgical procedures that are performed under general anesthesia. One major undesired consequence of general anesthesia is hypothermia, which is a reduction of the body's core temperature. Hypothermia causes physiologic diseration of all major body functions including that of cardiovascular and respiratory systems, nerve conduction, mental acuity, neuromuscular reaction time and metabolic rate. Countering these side effects is a major challenge both during the operation and particularly in the postoperative procedures and in intensive care units.

In open-heart surgeries, the treated patient is connected to a heart-lung machine during the open-heart phase of the surgery. However, during the period preceding this phase, it is important that the various physiological functions of the body will be in as best as possible condition prior to connection to the heart-lung machine. However, typically the cardiac index of the patient deteriorates during this period to levels below desired. That has an effect on the eventual recovery of the patient after the surgical procedure.

Generally, reduction in cardiac index is a major problem during surgical procedures performed under general anesthesia.

GENERAL DESCRIPTION OF THE INVENTION

The present invention provides a method and system, which bring to improvement in cardiovascular parameters and a cardiac protein marker of a patient undergoing a medical procedure under general anesthesia. This is a result, in accordance with the invention, from proper control of the body's core temperature. This control is achieved by a system comprising a heat exchanger which is in contact with the external body surface and employing a heating regime which takes into consideration the dynamic heat transfer properties of the body.

The term "improvement" or "improving" when relating to cardiovascular parameters means to denote improvement in one or more of such measured parameters as compared to patients undergoing a similar procedure with the body heat not being controlled in a manner as provided for in accordance with the invention. The purpose of such improvement is in essence to maintain the cardiovascular parameters as close as possible to normal, namely similar the level of such parameters in the individual prior to undergoing the surgical procedure.

The term "cardiovascular parameters" is used herein to denote measurable parameters of the cardiovascular system used to determine proper (or improper) operation of the heart and the vasculature. A very important cardiovascular parameter is the "cardiac output". The cardiac output is a measure of the pumping capacity of the heart (typically measured in liters per minute), and is an important measure of proper heart function. Usually the Cardiac Output is expressed in relation to the body surface area (BSA) as the Cardiac Index—L/Min/m$^2$. Another cardiovascular parameter is the systemic vascular resistance (SVR)—dynes-sec-cm$^{-5}$ which represents the cardiac afterload and is usually elevated as a result of hypothermia. This eventually necessitates augmentation of cardiac work to provide perfusion to body tissues. Cardiac troponine I (cTn-I) is a regulatory protein specific for the myocardium, the level of which is measured in the serum. The cTn-I level typically rises as a result of damage to the myocardium. cTn-I levels may significantly rise during a cardio-pulmonary bypass surgery.

The term "core temperature" is used herein to denote the temperature within the body, namely that of the internal organs and tissue. Core temperature is typically measured through the rectum but may also be measured by inserting probes through a variety of other body cavities, e.g. mouth, nasal, esophageal, bladder or ear temperature probes. The term "surface temperature" will be used to denote the temperature of the external body surface (which may be that of the skin or, where the skin has been damaged, e.g. in burn injury, that of the most external layers). It should be noted that the surface temperature may vary between different body portions. The surface temperature may be measured by a variety of temperature probes including, for example, an infrared sensor measuring infrared emission from a specific skin portion, probes attached to the skin such as thermal-couple devices, thermister, etc.

In accordance with a first aspect of the invention there is provided a method for improving cardiac paramaters, including, but not limited to cardiac index, systemic vascular resistance and Cardiac Troponin I in a patient undergoing a medical procedure under general anesthesia, comprising: contacting a substantial portion of the patient's external body surface, without covering the areas where surgical procedures are performed with a heat exchanger which can transfer heat to or absorb heat from the body surface; continuously measuring parameters from the body including at least the actual body core temperature (aBCT); and in a processor, receiving data signals corresponding to the measured parameters, comparing the aBCT with a desired body core temperature (dBCT) needed in order to maintain a desired cardiovascular parameters based on the aBCT/dBCT difference, emitting a control signal to control heat transfer properties of said heat exchanger.

In accordance with another aspect of the invention there is provided a system for improving the cardiac parameters, including, but not limited to cardiac index, systemic vascular resistance and the levels of Cardiac Troponin I of patients undergoing medical treatment under general anesthesia, the system comprising:

a processor controlled heating/cooling unit coupled to a flexible heat exchanger for contacting substantial portions of a patient's body surface and for transferring heat to or removing heat from said portions, said cooling unit having the ability to change heat transfer properties of the heat exchanger with said substantial portions:

at least one BCT-sensing device for measuring the patient's aBCT and emitting an aBCT data signal; and a control module for receiving data signals from measuring devices, comprising the aBCT data signal, and for emitting a control signal for controlling heat exchange properties of said heat exchanger as a function of the data signals and a dBCT needed in order to maintain a desired cardiovascular parameters.

The invention yields an improvement of cardiovascular parameters and the after load, which is a consequence of the controlled heating-induced vasodilatation or reduction in the vasoconstriction.

In accordance with one preferred embodiment of the invention the system comprises at least one sensing device for measuring a parameter indicative of the heat transfer dynamics (HTD) between the body's surface and the body's core. Thus, in accordance with this embodiment, such a parameter is continuously measured and a data signal corresponding to this parameter emitted from the device is fed into said processor, and this signal is factored in the control signal emitted by the processor.

The term "substantial portion of the body surface" means to denote such a portion which is sufficient to achieve a sufficient degree of heat exchange to yield the dBCT. Typically, such a substantial portion will be at least 40%, preferably at least 50% of the body's surface.

The heat exchanger may either be provided with an internal heat or cold producing capability e.g. including a Peltier effects modules, or the heat exchanger may be linked to at least one source of cold and/or hot fluid, which fluid then circulates between such source and the heat exchanger to transfer heat/cold between the exchanger and the source. The heat exchanger is typically designed as a flexible, modular garment for wearing over portions of the patient's body, typically covering major portions of the patient's torso, legs, arms, shoulders and at times also portions of the patient's skull.

A preferred heat exchanger for use in accordance with the invention is such that leaves the front, central portion of the chest exposed to permit the surgeon access to the surgical target field. Typically, the garment is designed to leave the internal thigh surfaces exposed to permit removal of arteries which are needed in the case of bypass surgery. The garment in accordance with this preferred embodiment, which also forms an independent aspect of the invention, is typically provided with adhesive strips or flaps to permit direct adhesion to the skin for fixing of the garment in situ. Such a garment is suitable, for example, for use in open heart surgery.

The control of the heat exchange properties of said heat exchanger may involve change of the heat transfer properties between the heat exchanger and the body surface which may be achieved, for example, by changing the heat conductance parameters between the body's surface and the skin, e.g. by pumping or removing air into or from air pockets disposed between heat radiating/heat absorbing members within the heat exchanger and the skin; or preferably, by changing the temperature of the heat exchanger, which may either be a reduction in the extent of heating or cooling, halting the heating or cooling operation, or reversing the heating or cooling operation into cooling or heating, respectively In reversing, the heat exchanger acting first as a heat source will be switched to become a heat sink, or vice versa, thus reversing the direction of heat transfer.

The heat exchanger may, for example, comprise electric heating/cooling devices, e.g. Peltier devices and others. However, in accordance with a preferred, non-limiting, embodiment of the invention, the heat exchanger is of a kind having one or more conduits or fluid transfer space defined there for passing the temperature control fluid therethrough. The fluid, which is typically, though not exclusively a liquid, e.g. water, may be driven through the conduits or space by a pump or any other suitable device therefor. Such fluid thus circulates between the heat exchanger and a heat and/or cold source. The heat exchanger is typically flexible to allow it intimate contact with a body surface for efficient heat transfer therewith.

In addition to the above noted measuring devices (the BCT sensing device, the device for measuring a parameter indicative of said HTD), the system may further comprise one or more devices for measuring temperature of the circulating fluid and for emitting data signal relating thereto to the controller. At times, where the system comprises two or more such devices, at least one of which may serve as an inlet temperature sensing device for measuring temperature of the fluid as it enters the at least one conduit or fluid transfer space, and at least one other may serve as an outlet temperature sensing device for measuring temperature of the fluid as it exits the at least one conduit or fluid transfer space. The temperature drop ($\Delta T$) between the garment's inlet and the outlet is a very good indicator of said HTD, since this information, together with information on the fluid's flow rate, permits an accurate calculation of the heat transfer between the heat exchanger and the body, which depends on said HTD. Thus, in accordance with a preferred embodiment said $\Delta T$ and the fluid flowrate are used as an HID-indicating parameter.

The heat exchanger of the invention is typically a garment which is worn over a portion of the patient's body. Typically, the garment may be designed so as to cover at least about 40%, preferably at least about 50% of the body's surface. In this way, the system of the invention effectively stabilizes a patient's body temperature, at a desired body core temperature, within a minimal tolerance. A currently preferred embodiment of the invention is the application of the system for control of body temperature of patients during or after cardiac surgery. For this purpose the heat exchanger, typically in the form of a garment, may have a variety of openings permitting access for the performance of the required procedures, for parenteral administration of drugs or fluids or for drainage of body fluids. (e.g. excretions or blood).

As will no doubt be appreciated, a heat exchanger in the form of a flexible, modular garment may typically be designed to have various forms and sizes, to meet specifications of patients of various ages, weights, heights or gender to meet the specific requirements of the desired surgical procedure.

The sensing device for measuring a skin parameter indicative of said HTD (hereinafter referred to at times as "HTD device"), may, in accordance with the one embodiment, include a device for measuring a temperature at a skin portion proximal to a skin portion on which the heat exchanger is applied. The HTD may then be determined for example, by either one or both of (i) determining the rate of temperature change at said skin portion following heating or cooling of adjacent skin portions by the heat exchanger, or (ii) by assessing the rate of change of temperature difference between the skin portion and the core during heating or cooling of the body.

Said HTD device may, in accordance with another embodiment of the invention, consist of the aforementioned at least two sensing devices for measuring temperature of the fluid as it enters the at least one conduit in the heat exchanger and the temperature as it exits from the at least one conduit. The controller, thus receiving at least two data signals relating to the measured temperature, then calculates said HTD based on the inlets or outlet temperature differential and on the fluid flow rate, which is either determined by the controls or measured by ant appropriate measuring device.

In accordance with other embodiments, said HTD device is adapted for measuring a parameter indicative of said HTD, which parameter may be one of a variety of skin and peripheral blood flow parameters. These may be determined by many techniques, e.g. by echo Doppler signal techniques, skin conductance, peripheral blood pressure, skin temperature, skin color, etc.

The determination of the heat transfer dynamics (HTD), and taking the heat transfer dynamics into consideration in the heat control regime of the patient is an important feature of the method and system of the invention. Specifically, when the HTD parameters point to the occurrence of vasoconstriction, any applied cooling should be temporarily halted or reduced. At times, it is advantageous also to reverse the heat transfer mode, temporarily heat in a cooling mode. This means that a cooling mode will involve occasional heat pulses timed and patterned according to said HTD.

The system may have a user interface permitting a user to enter a dBCT, namely a temperature set point of the system. The user interface may farther comprise control means allowing selective operation of the system in either an automatic mode, namely in a mode permitting both cooling and heating depending on the direction or deviation of the aBCT from the dBCT. In addition, the control means may also typically allow selecting a heat only mode or a cool only mode.

Typically, the heating will be limited so that the temperature at the surface of the heat exchangers, which is in touch with the body surface, will not exceed maximum temperature, e.g. a temperature of about 40° C. and not to fall below a minimum temperature, e.g. about 15° C.

In order to be effective in cooling or heating, The heat exchanger garment has to be fitted onto the patient's skin. At times, there is a need to wear such a garment for prolonged periods of time, and this may give rise to a risk of pressure wounds. In order to circumvent this problem, in accordance with one embodiment of the invention, the heat exchanger has two or more patiently flow-controlled flow sub-systems, and these sub-systems may then be used intermittently, namely, one system being inflated with fluid and used, while the other being deflated and thus not exerting pressure on the skin; and vice versa. In accordance with another embodiment, the fluid transfer to the garment is temporarily halted for periods of several seconds to minutes in order to reduce the pressure onto the skin thus reducing currents of pressure.

In accordance with one embodiment of the invention, the system comprises an electric in-line fluid heating/cooling unit and the circulation fluid is directed to flow through said unit for heating or cooling. Heating or cooling of the fluid in such a unit may also be achieved by means of an auxiliary circulatory heat transfer fluid through the intermediary of a heat exchanger within said unit. In accordance with another embodiment, the system comprises at least one cold fluid reservoir and at least one hot fluid reservoir and comprises a fluid flow control system for selectably drawing fluid from these reservoirs. One advantage of having independent hot and cold fluid reservoirs, is that the switching between heating and cooling modes can be rapid.

In a system comprising independent hot fluid and cold fluid reservoirs, the flow control system is preferably adapted to permit return fluid to flow back into the reservoir from which it was drawn. It is preferred that during switching from a cold to hot fluid or vice versa, the original fluid will flow initially to the reservoir from which it was drawn, and only after the warm fluid has been exploited will the returned fluid be directed to the other reservoir. Otherwise, the cold reservoir may be heated or the hot reservoir cooled. This may be achieved by having a temperature sensing device measuring the temperature of the fluid flowing out of the heat exchanger and only when the device measures an abrupt temperature change, will the flow control system begin to direct the fluid to the new reservoir.

In order to understand the invention and to see how it may be carried out in practice, a preferred embodiment will now be described by way of a non-limiting example only, with occasional reference to the annexed drawings:

BRIEF DESCRIPTION OF THE DRAWINGS

FIG. 1A is a garment useful in the method and system in accordance with an embodiment of the invention.

FIG. 1B is an enlargement of the region marked "B" in FIG. 1A with the two external layers being partially separated for illustrative purposes.

FIG. 2 illustrates a top view of a laid-open garment, for use in the system in accordance with an embodiment of the invention.

(FIG. 11B is continuum of FIG. 11A).

DETAILED DESCRIPTION OF PREFERRED EMBODIMENTS

Figure 3:
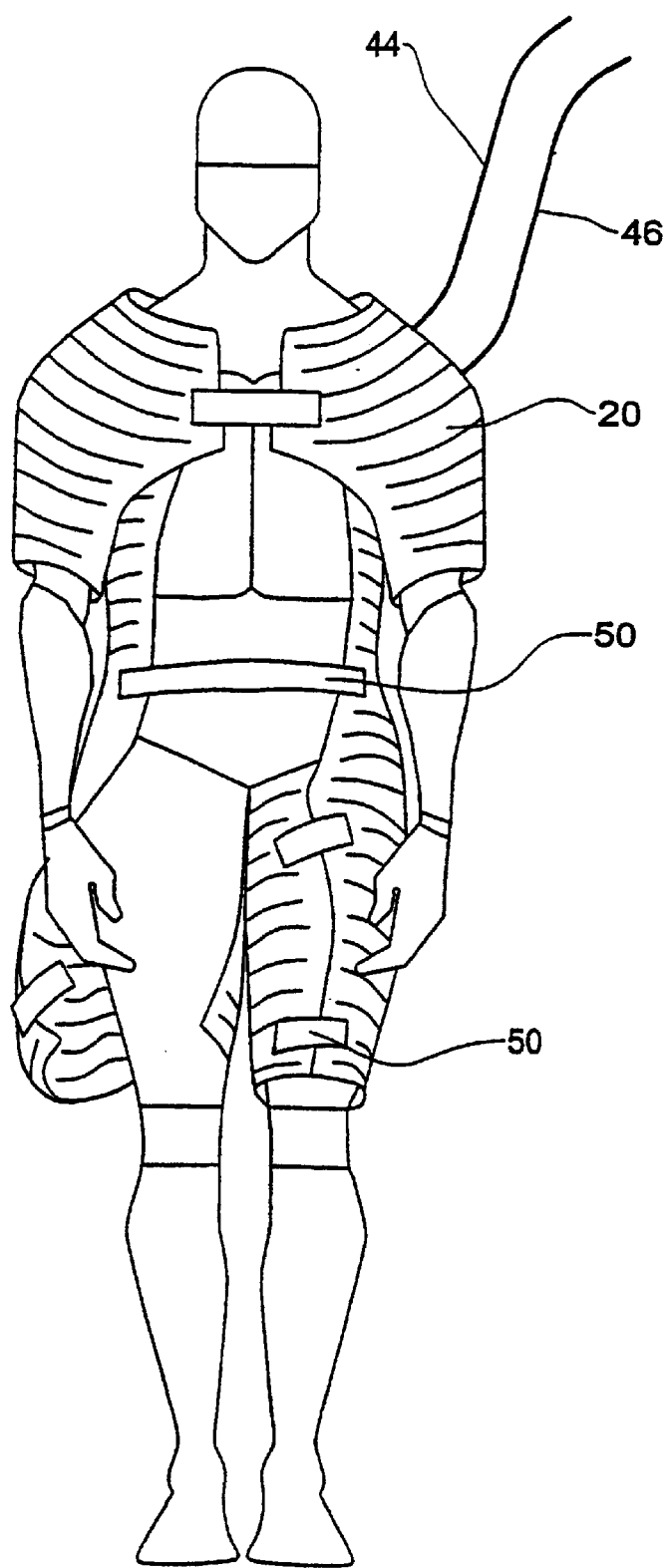
FIG. 3 is a schematic illustration of the garment of FIG. 2, applied to a patient.

A top view of a garment 2 in accordance with one embodiment of the invention shown in an open layout can be seen in FIG. 1. Garment 2 is designed for fitting over a person's torso. Garment 2, as can specifically be seen in FIG. 1B, is formed with two external layers 4 and 6 defining between them a fluid passage space 7. The garment is provided with a fluid inlet 8 and a fluid outlet 10 for respective fluid ingress and egress into and out of the fluid passage space. The garment is provided with a partition 12 which defines a fluid flow-path which is represented schematically by arrowed line 14. This fluid is typically water but may also be any other suitable liquid, e.g. alcohol, oil, etc., and may also, in other embodiments be a gas, e.g. air.

As can further be seen in FIG. 1B, the garment is formed with a matrix of welded points 16 where the two external layers 4 and 6 of the garment 2 are welded one to another. In use the pressure of the fluid forces the two layers away from one another filling fluid in the space between the welded points. The welded points ensure the structural integrity of the two layers and further ensure some resistance to fluid flow and consequently substantially even distribution of fluid flow through the garment's entire fluid passage space 7. As will no doubt be appreciated, the internal structure of the garment is but an example. By other embodiments the garment may comprise two external layers sandwiching a porous matrix between them: may comprise tubes or other conduits embedded or defined therein by welded lines: etc.

A top view of a garment in accordance with another embodiment shown in open layout, and generally designated 20, can be seen in FIG. 2. The garment 20 has openings 22 and 24, which allow, when the garment is fitted on a person, access to the underlying skin portion, e.g. for skin temperature measurements, for injection, etc. Rather than openings 22 and 24 the garment may also be provided with flaps serving a similar purpose. The garment is provided with several cuts 28, 30 and 32 for fitting of the garment on the patient, as can be seen in FIG. 3. The garment which may have a similar internal structure to that shown in FIG. 1B, is formed with weld lines 34A, 34B, 35, 36A and 36B which together define a fluid flow path as represented by arrowed lines 37A, 37B, 37C and 37D extending between the fluid inlet 44 and outlet 46. In this case, the garment is structured such that the chest and abdominal portion of the patient are left open, thus rendering this garment suitable for chest and abdominal surgery. For other surgical applications, the garment may assume a variety of different shapes. In addition, the garment may also be provided in various sizes for fitting patients of different weights, gender, age, etc.

The garment may be made of a variety of different materials including fabrics, plastic materials, etc. The garment should preferably be flexible and elastic to allow it to fit over an patient's body. The outer layer of the fabric may be coated with a heat insulating material, to prevent heat transfer to the external environment. In addition, the garment may have an internal soft lining such as felt, in order to avoid occurrence of pressure wounds.

Furthermore, as will be explained with reference to FIG. 5, the garment may be provided with an internal fluid absorbent layer.

The garment may be made for multiple use, or occasionally may be made disposable. The garment made for multiple use should be made of such materials as to allow its sterilization by any one of a plurality of sterilization means known per se.

Figure 4:
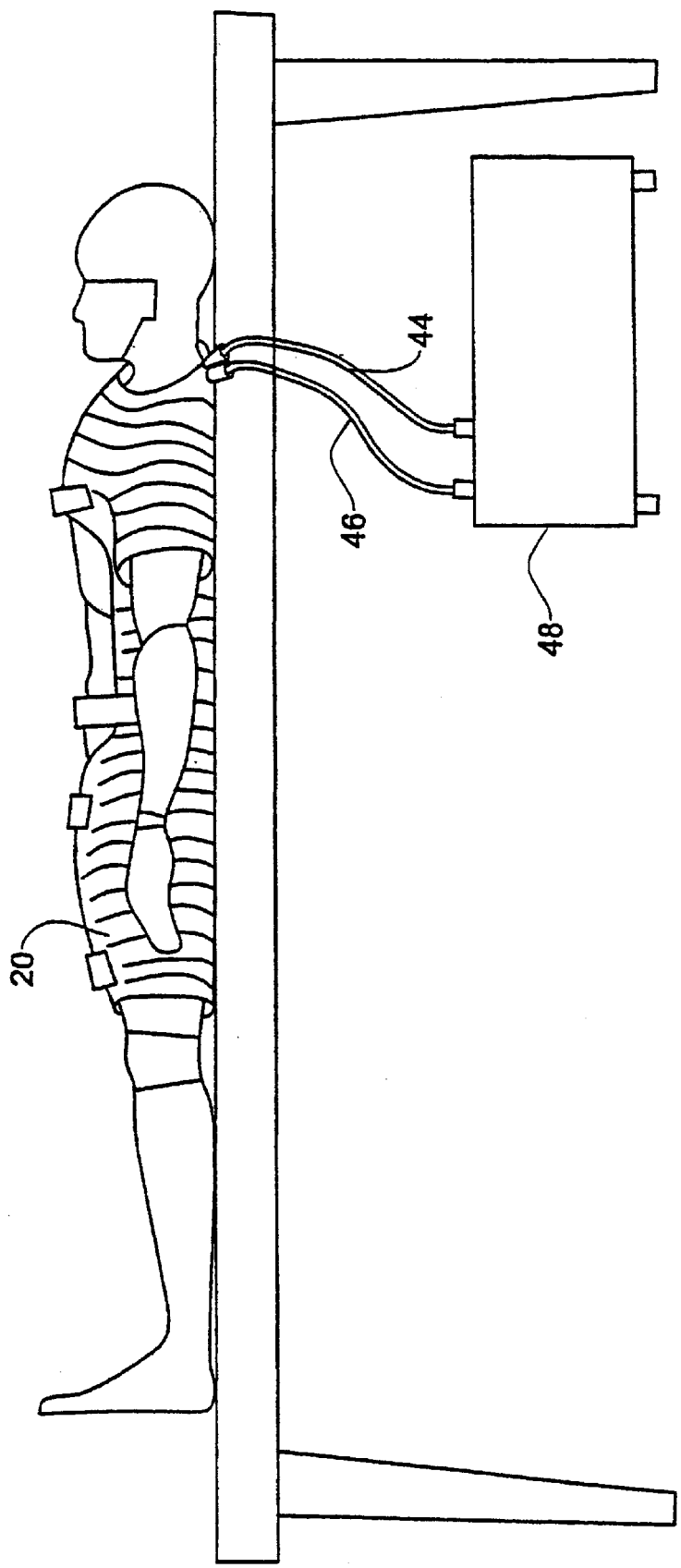
FIG. 4 is a side elevation of the patient with the garment of FIG. 3.

As can be seen in FIGS. 2–4, fluid inlet/outlet tubings 44, 46 are connectable to a liquid temperature control unit 48 (seen in FIG. 4).

In order to allow easy fixing and removal of the garment, it is typically provided with detachable fixing means, such as a hook and pile (e.g. Velcro™) type attachment members 50.

Figure 5A:
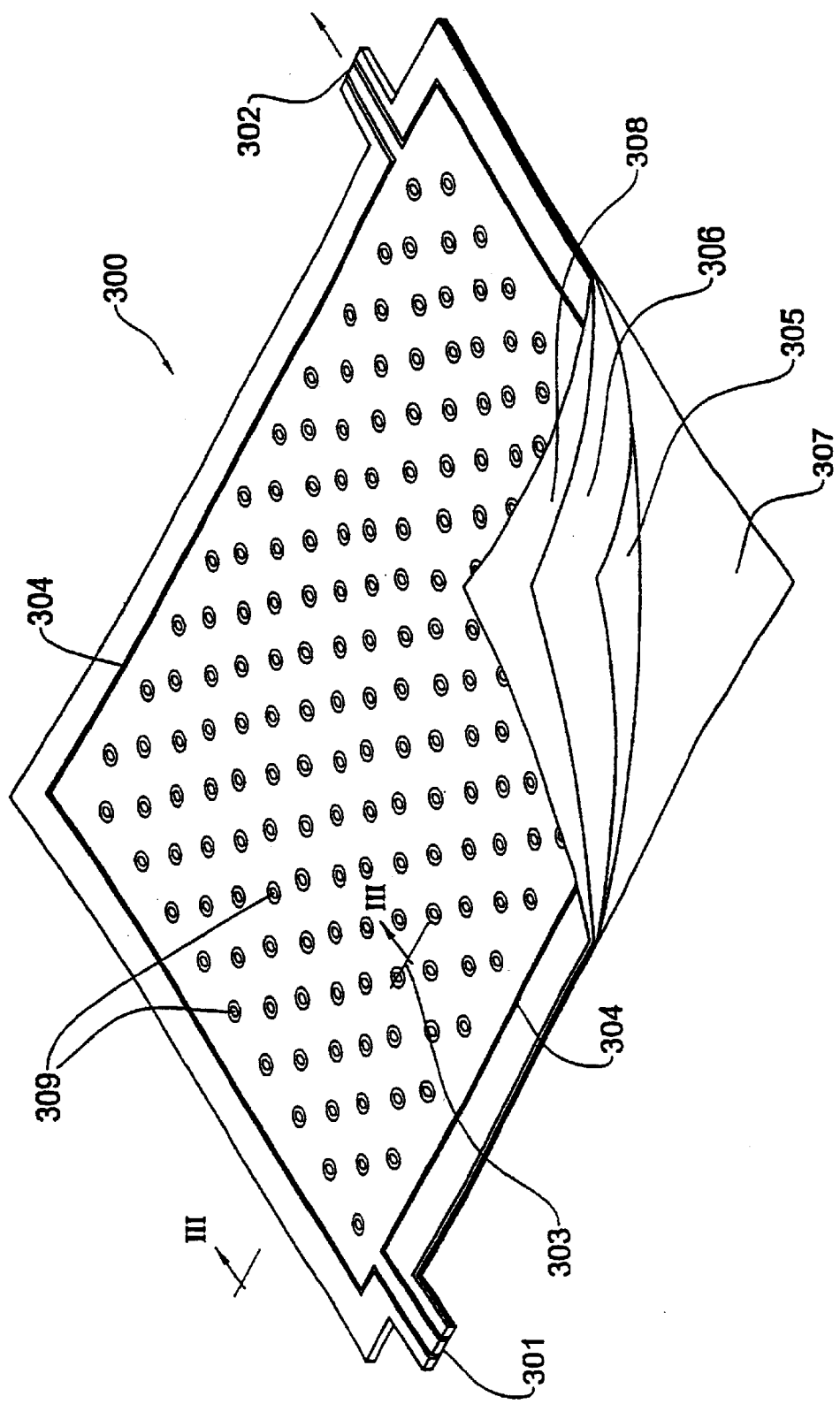
FIG. 5A shows a heat exchanger of a kind useful in certain embodiments of the invention, with one comer being opened to illustrate its four-layered construction.
Figure 5B:
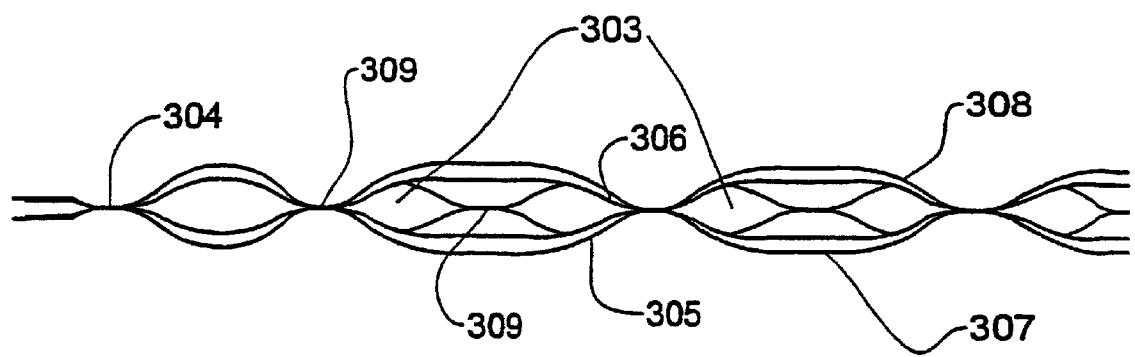
FIG. 5B is a cross-section through lines III—III in FIG. 3A.

Reference is now being made to FIGS. 5A and 5B showing a heat exchanger 300 having a fluid inlet 301 and a fluid outlet 302 for the transfer of heat exchange fluid through internal space 303 formed within the heat exchanger and confined by weld lines 304. Fluid inlet 301 and fluid outlet 302 are connected, respectively, to a fluid supply tube and to a fluid drainage tube which are in turn connected to a system which supplies the cooling fluid.

Fluid space 303 is defined between two fluid tight sheets or films 305 and 306 which are overlaid by respective outside layers 307 and 308. Sheets 305 and 306 are typically polyethylene sheets such as Metallocene PE (manufactured by Dow Elanco, USA) and layers 307 and 308 are made of non-woven polypropylene spunbond fabric of the characteristic weight of about 30–40 gm/m$^2$. As will, however, be appreciated, the external layers can be made to other specifications to meet any desired characteristics. They may have different characteristic weights, different textures, etc., to provide different levels of flexibility and insulation. The four layers are welded together typically by R.F. (radio frequency) welding, at the edges 304 and at a plurality of weld points 309. The weld points 309 are typically arranged in an orderly fashion in an array, with the distance of well points being typically within the range of about 8 to about 20 mm from one another.

The overall rectangular design of the heat exchanger as seen in FIG. 5A is a mere example and the heat exchanger may be formed into various desired forms and shapes depending on the intended need. In accordance with one preferred embodiment of the invention, the body heat control garment in accordance with the invention is formed with a heat exchanger having the characteristics of the heat exchanger of the kind shown in FIGS. 5A and 5B. For such an application, the external non-woven spunbond fabric provides a physiologically compatible contact interface with the skin and furthermore, its somewhat hydrophilic properties permit absorption of liquids including sweat, blood, or other body fluids.

Figure 6:
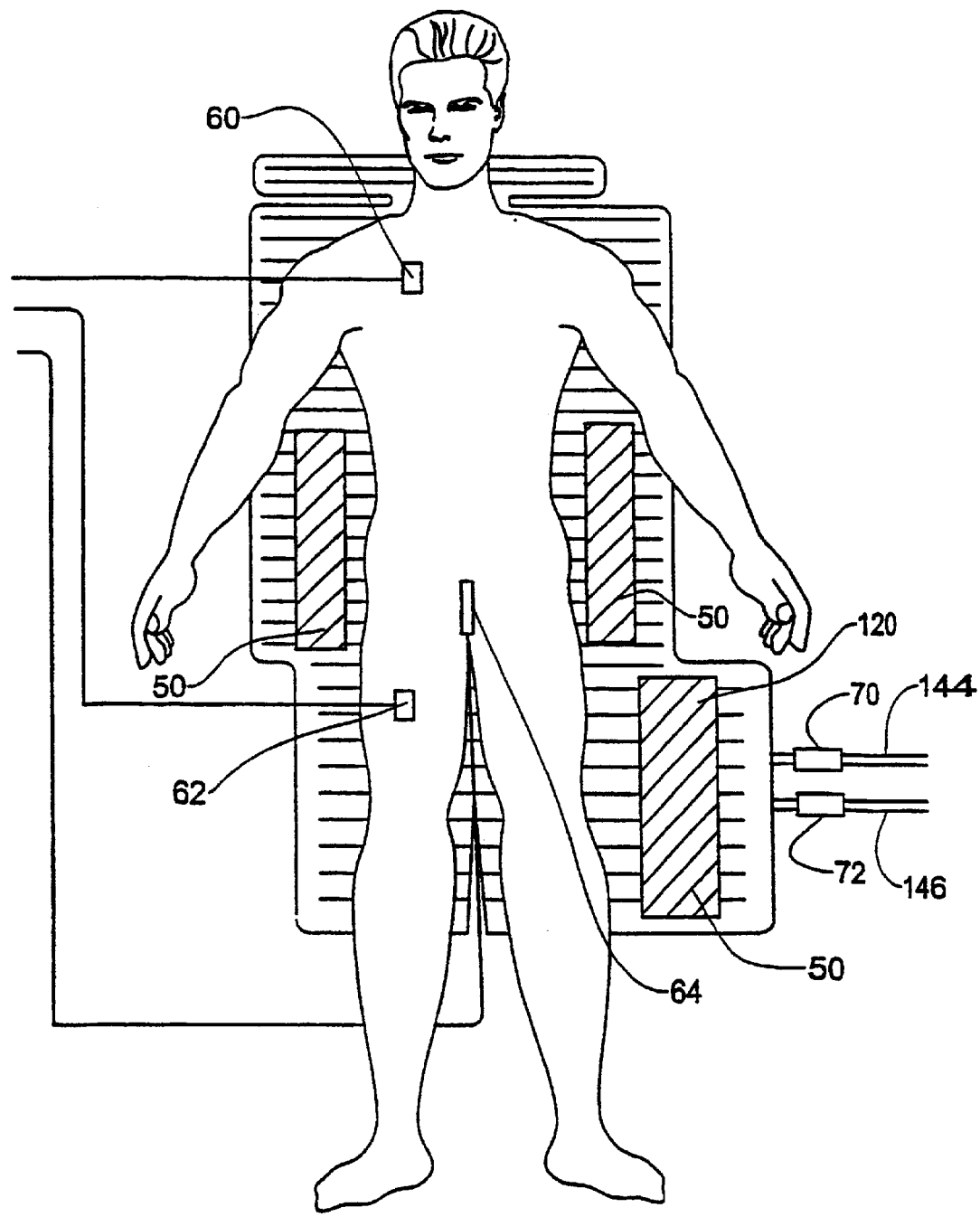
FIG. 6 shows a garment useful in accordance with another embodiment of the invention, in an open state with the patient lying thereon provided with an adhesive matrix.

FIG. 6 is a planar view of a garment 120 in accordance with another embodiment of die invention, still in an open position, prior to fixing it over the patient's body. In this figure, like reference numerals to those of FIGS. 2–4 were used, with a "100" index (namely with a "1" prefix) and the reader is referred to the description relating to FIGS. 2–4 for their explanation. Further seen in FIG. 6, are matrices 50 which are made of an absorbent material. Typically, such a matrix has a fluid permeable layer, and a hygroscopic material capable of absorbing liquids and retaining them within. Such matrices of liquid absorbent properties, are readily known in the art, and a detailed description of their structure goes beyond the present writing.

Also seen in FIG. 6, are skin-temperature sensing probes 60 and 62 and a rectal temperature probe 64 for measuring core temperature. In addition, other types of temperature measuring devices may be provided, e.g. an intra-ear temperature measuring device, an infrared sensor for measuring skin temperature, an oral temperature measuring device for measuring core temperature, etc. As explained above, the skin temperature is measured, in accordance with one embodiment of the invention, in order to determine the heat transfer dynamics (HTD) of the skin. For the same purpose, as an alternative to measurement of skin temperature, other parameters may be measured which include skin color, skin conductance, peripheral blood pressure, temperature drop of the heating or cooling fluid (as will also be outlined below), as well as any other parameters which can give an indication of occurrence of vasoconstriction or vasodilatation.

In addition, advantageously, temperature sensing devices 70 and 72 for measuring inlet and outlet fluid temperature may also be provided. Such information may also be utilized for the rate of heat transfer between the heat exchanger, namely the garment, and the skin in order to assess the HTD.

Figure 7:
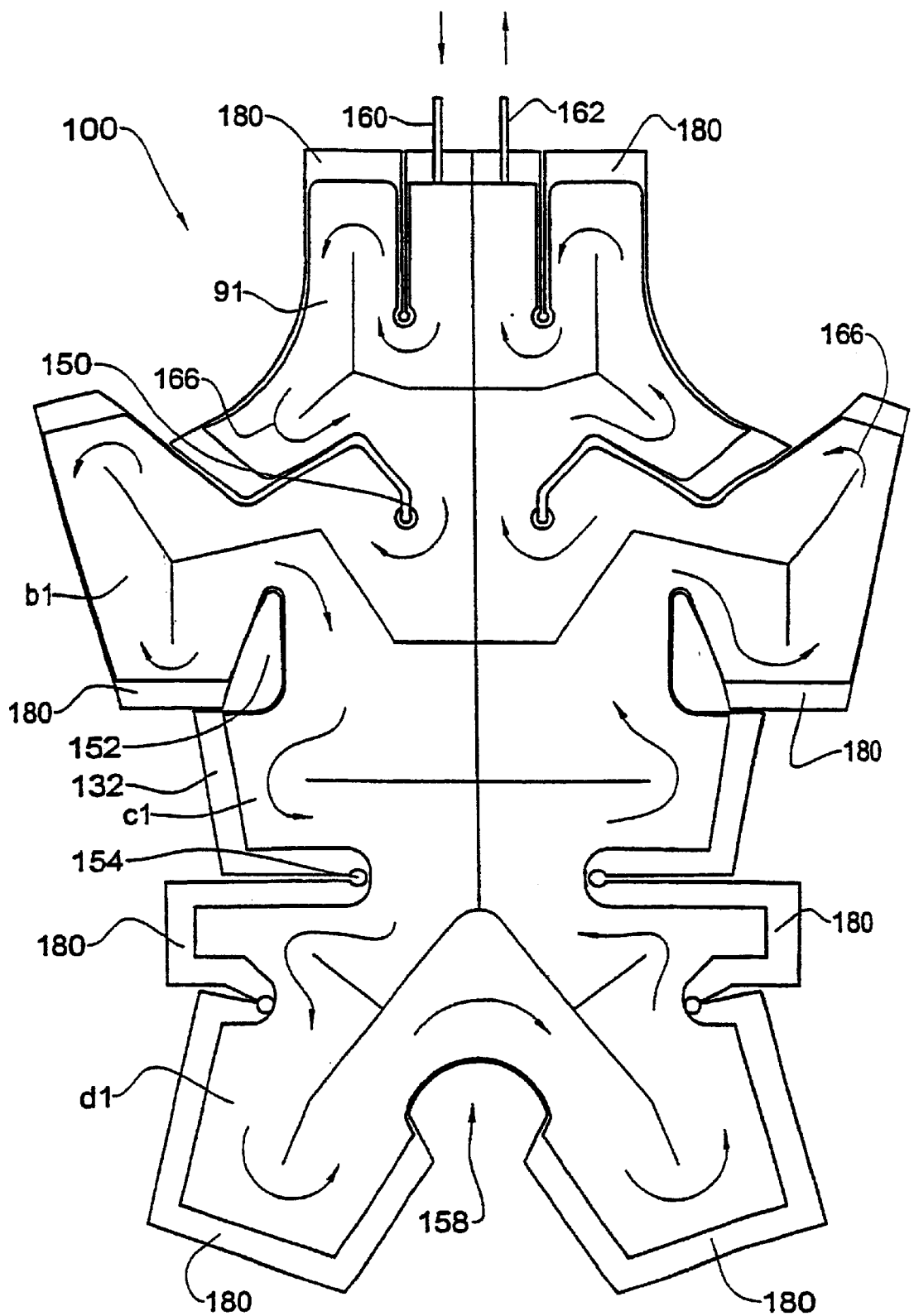
FIG. 7 is a top planar view of a garment useful in accordance with another embodiment of the invention.

Reference is now being made to FIG. 7, showing a garment 100 in accordance with another embodiment of the invention. In this figure, meant to illustrate the overall shape of the garment, the well line and the liquid flow path as illustrated in FIG. 2 has been omitted. This garment is specifically intended for use in cardiac surgery, e.g. coronary artery bypass surgery.

Garment 100 has a heat control liquid inlet 160 and a liquid outlet 162 (as will no doubt be appreciated the inlet and the outlet may be interchanged) leading into an elongated section 164 which during operation lies beneath the neck and head of the patient. The garment has two flaps 166 foldable over the patient's shoulders to cover a portion of the patient's chest; two sections 168 for fitting over the patient's arms; two sections 170 foldable over and enveloping the sides of the patient's torso, a hip section 172 [is this correct?] and two sections 194 for enveloping a portion of the patient's leg. In operation, the patient is placed over garment 100 with all sections being folded to envelope respective body portions leaving the central area of the chest and stomach exposed to allow access for surgery.

Various sections of the garment are provided with adhesive flaps or strips 200 covered with a glue which can adhere to the patient's skin. The adhesive is preferably such resistant to aqueous liquids and the chemicals and solvents, e.g. disinfectants, used during the operation.

Figure 8:
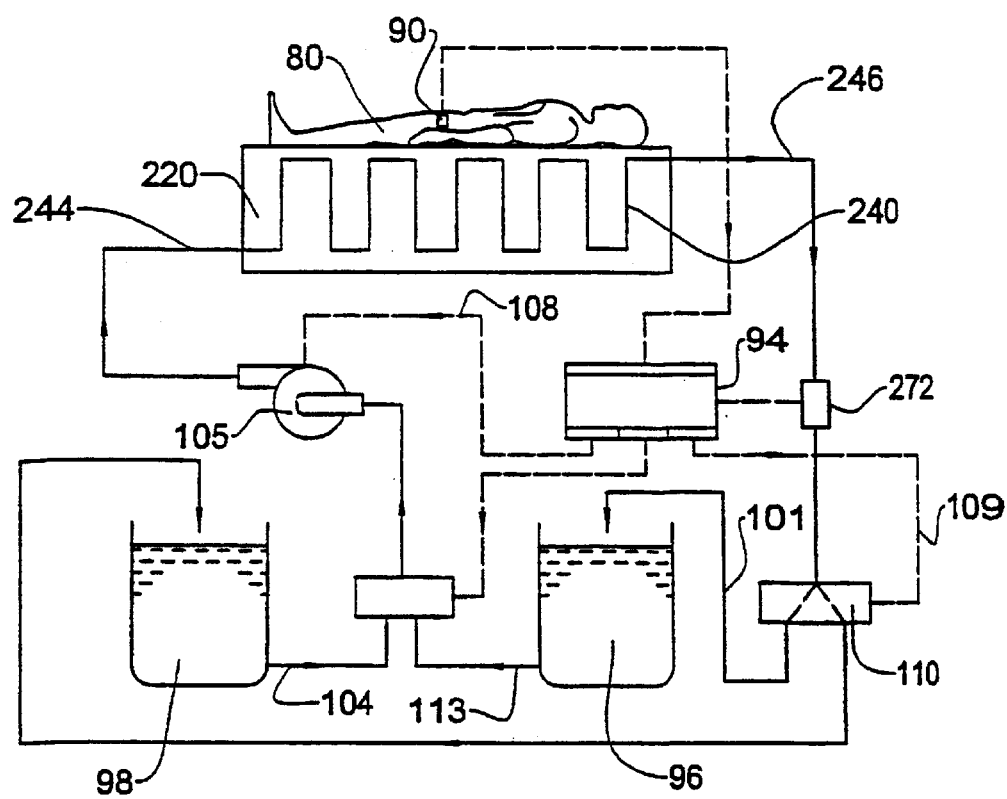
FIG. 8 is a schematic general illustration of a system in accordance with the invention.
Figure 9:
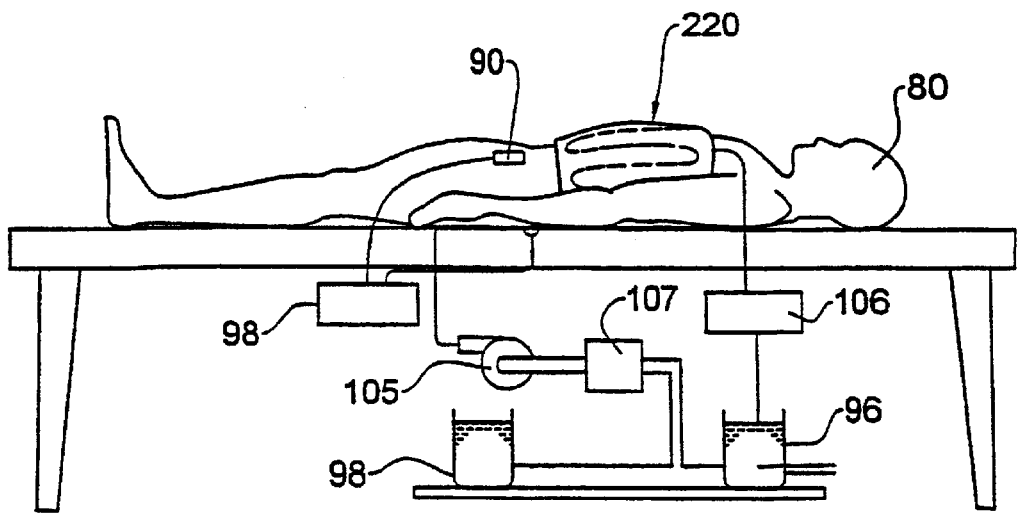
FIG. 9 is a schematic side elevation of the system of FIG. 8.

A schematic representation of the system in accordance with another embodiment of the invention can be seen in FIGS. 8 and 9. A patient 80 as shown herein is provided with a garment 220 (shown schematically as a rectangle in FIG. 8). Garment 220 is provided with a fluid inlet 244 and outlet 246 and with a continuous fluid conduit or a continuous porous space 240 between them, embedded in garment 220. A plurality of sensing devices shown herein schematically as component 90, transmit data signals reflecting the patient's physiological parameters, are transmitted to controller 94.

The system of this embodiment is adapted for both heating or cooling the patient. By one embodiment, hot fluid and cold fluid are provided from respective, independent hot and cold fluid reservoirs 96 and 98. Each of the reservoirs has respective fluid inlets 101, 102 and respective fluid outlets 103, 104. The system is provided with a pump 105 for propelling fluid within the system.

The system is provided with two flow control valves 106 and 107, for selectively transferring return fluid to or drawing fluid from one of the two reservoirs. Pump 105 and flow control valves 106 and 107, are electrically operated by controller 94 through command lines, 108, 109 and 110, respectively.

When switching from a heating mode to a cooling mode or vice versa, the flow control valves are switched accordingly. In accordance with one embodiment of the invention, the fluid outlet 246 is provided with a heat sensor 272 which allows switching of the returning fluid from one reservoir to another only upon sensing an abrupt temperature change by sensing device 272, which then transmits a data signal to controller 94 which in turn causes flow control valve to switch. The arrangement is such that the first flow control valve to be switched will be valve 107 and if, for example, the switch was from a cold fluid to a hot fluid, valve 106 will continue to direct the return fluid into reservoir 102 and only upon registering an abrupt temperature drop by sensor device 272 will be return fluid be channeled to reservoir 96.

Figure 10:
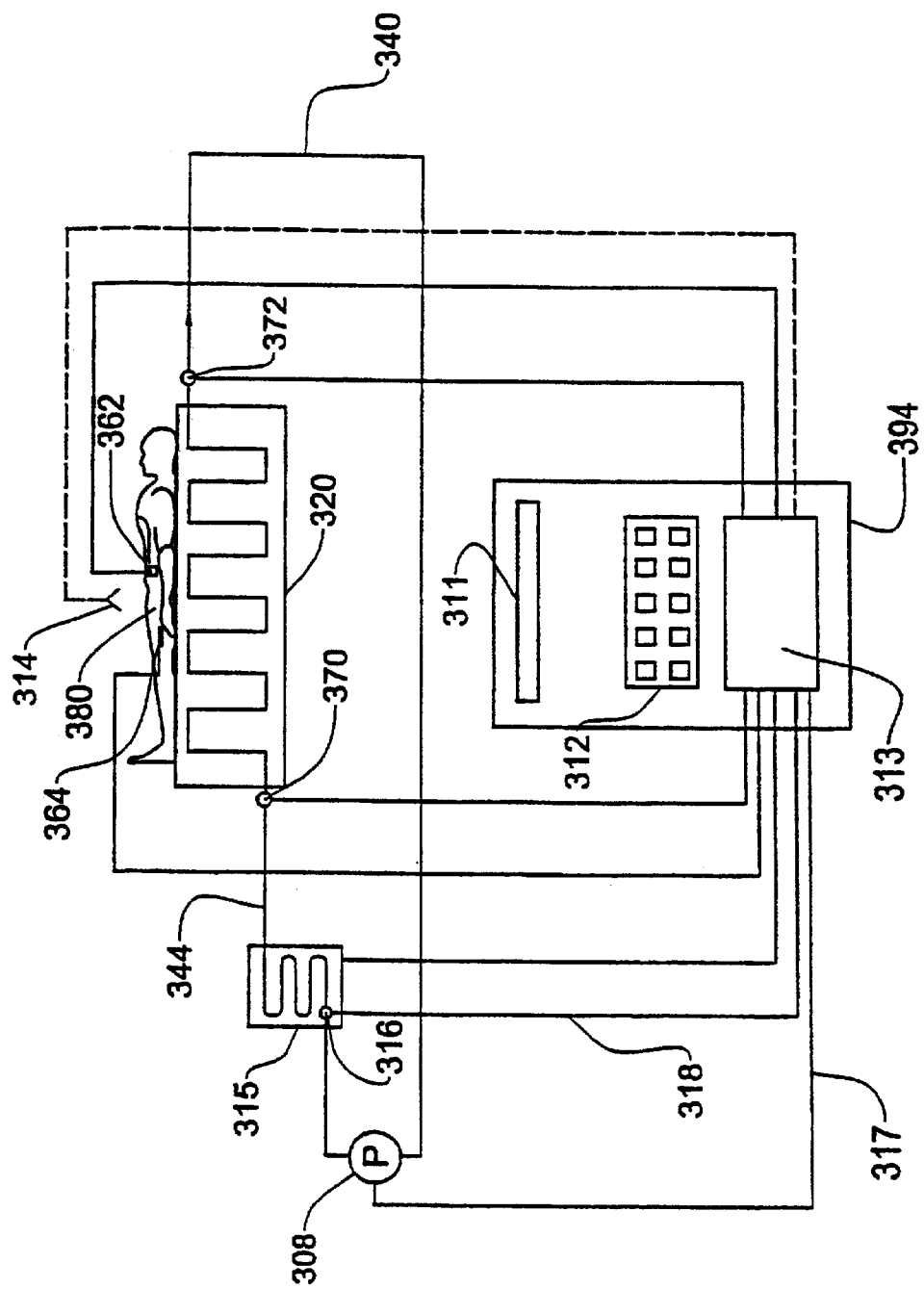
FIG. 10 is a principal schematic illustration of a system in accordance with another embodiment of the invention.

In other embodiments, such as that shown in FIG. 10, heating and cooling of the working fluid is carried out "on-line" by a heat pump operating as heater/cooler unit. Such a unit which may, for example, be provided with Peltier effect heat pumps, may easily be controlled to either heat or cool the fluid passing therethrough.

A schematic description of a system in accordance with an embodiment of the invention can be seen in FIG. 10. Controller 394 is provided with a display 311 to display the registered parameters, e.g. measured core temperature, the measured skin temperature, the desired core temperature, flow rate, fluid temperature, etc. In addition, controller is provided with a control panel 312 and a processor 313. The processor 313 receives data signals from all sensing devices (core temperature measuring device 364, skin temperature measuring device 362, an optional infrared skin-temperature measuring device 314, and others). In addition, the processor also receives temperature data from inlet and outlet fluid temperature sensing devices 370 and 372 and temperature registered in heating/cooling device 315 by means of a sensor 316. Device 315 may for example be a Peltier effect heat pump, as known per se. In addition, the controller controls the flow rate of pump 308 via command line 317 and controls the temperature of device 315 through line 318.

On the basis of the various data signals registered by the processor, and implementing various algorithms designed in accordance with the general teaching of the invention, e.g. that exemplified below, the flow rate of the fluid and/or the temperature of the fluid may be controlled. Various servo loops may be implemented through processor 313 for proper control of the various parameters.

Figure 11A:
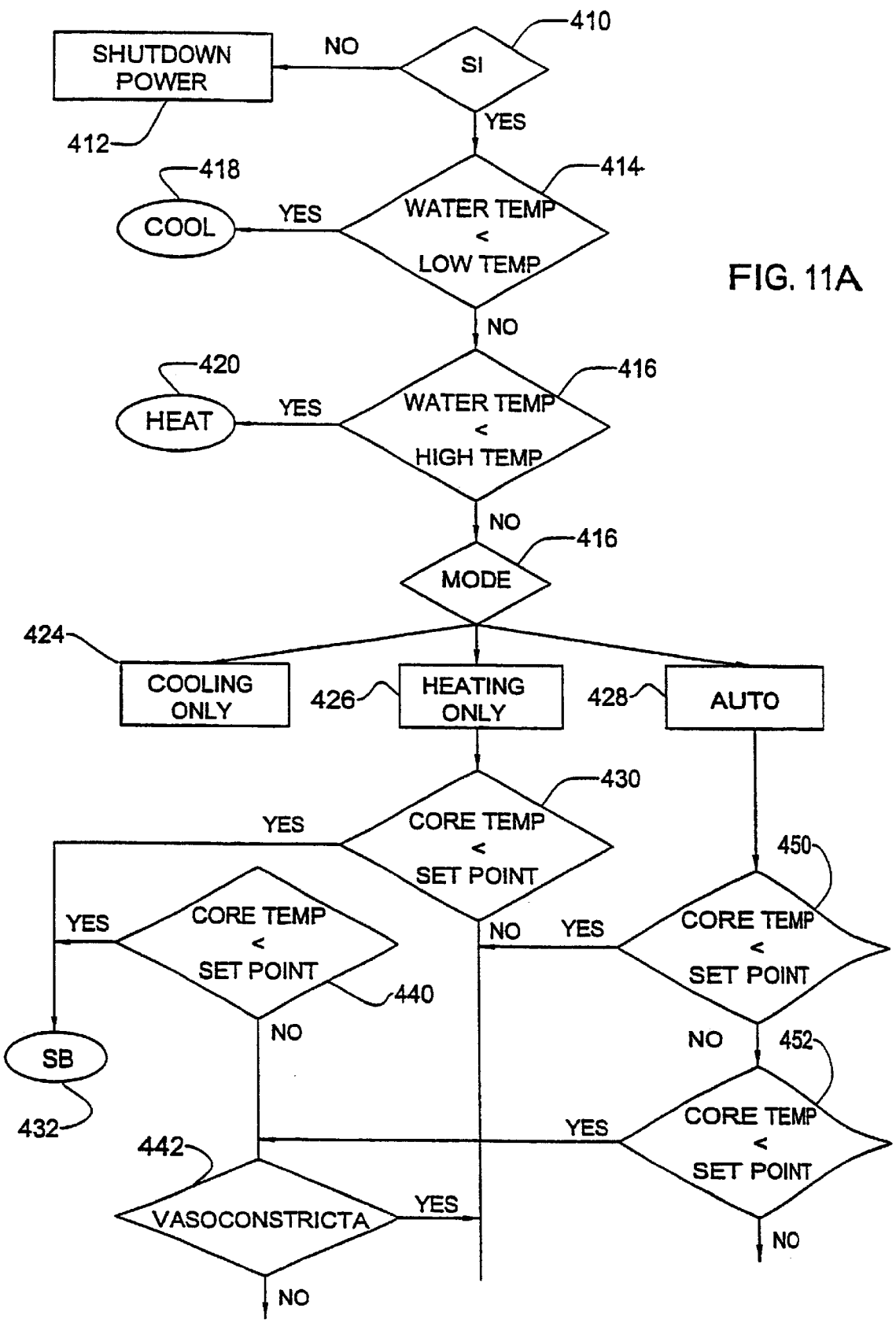
FIGS. 11A and 11B show a schematic block diagram of the algorithm operating in the system in accordance with one embodiment of the invention.
Figure 11B:
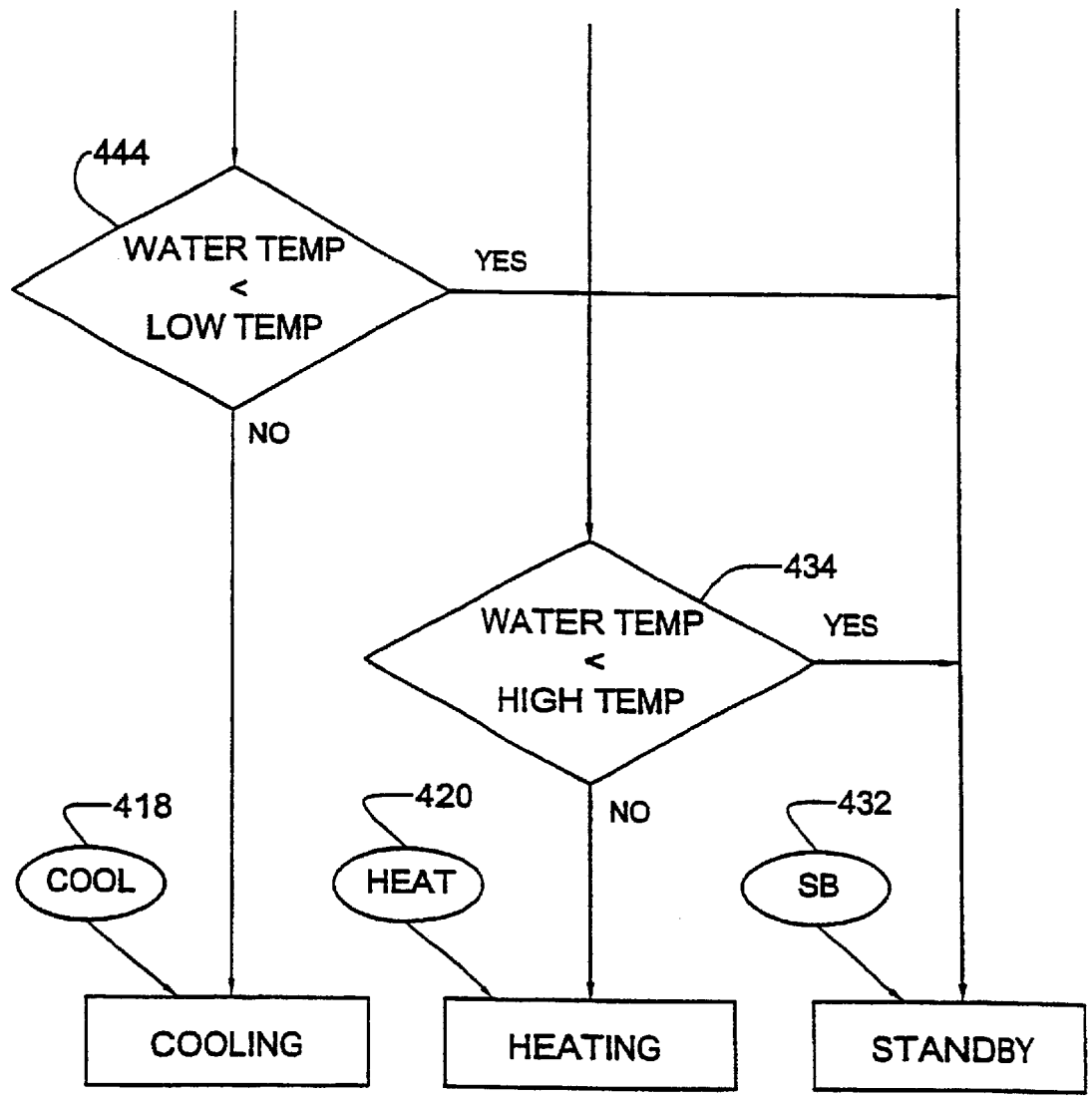
Figure 12:
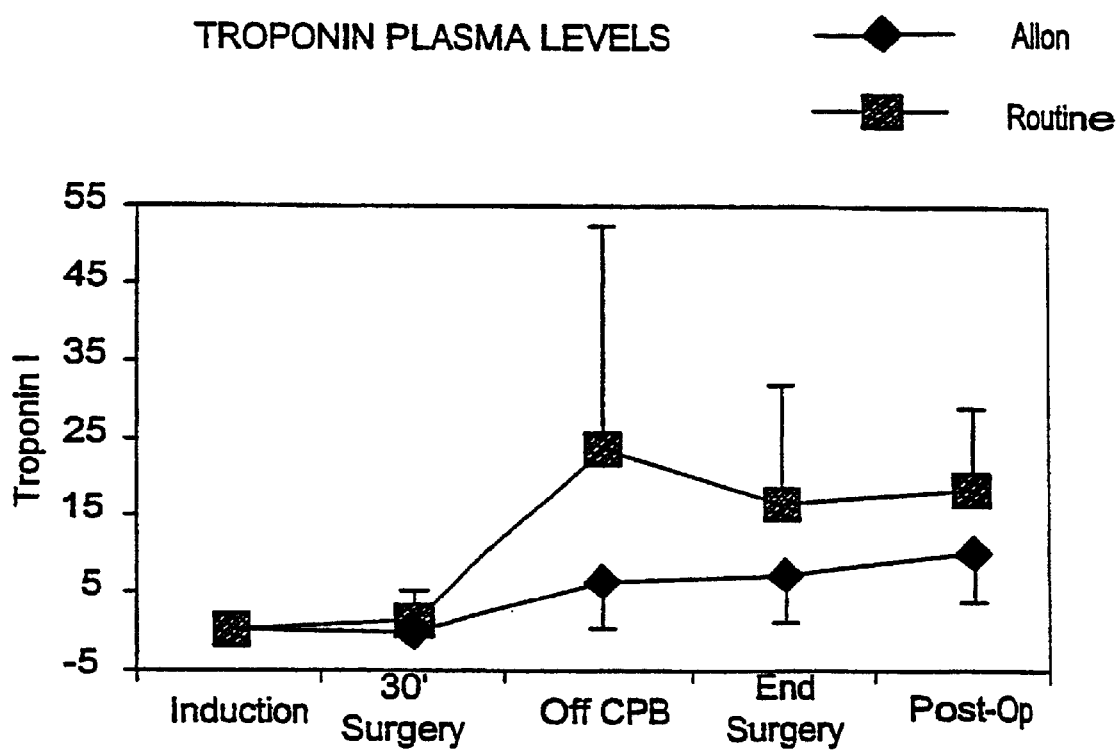
FIG. 12 shows results of the level of Troponin I during coronary artery bypass surgery with a system of the invention ("ALLON") as compared to a routine procedure.

FIG. 11A and 11B show an algorithm, by way of block diagram, of the various computational steps of the algorithm operating in a processor in accordance with the embodiment of the invention. Contrary to previous figures, the reference numerals used in this figure have no bearing to previously used reference numerals.

In a first decision step 410 the system is initiated and integrity is checked. If the system detects a fault, in any of its components, a system shut down sequence 412 is initiated. In the initiation step, the various operational modes are set. These may be automatic, heating only or cooling only modes.

Other parameters which may be set by the user are minimal and maximal permitted temperature of the heat transfer liquid, typically water to prevent tissue damage as well as discomfort to the patient, particularly when not under general anesthesia.

In the next two decision making steps 414 and 416, the actual water temperature (designated in the figure as "WATER TEMP") is compared to the maximally allowed water temperature ("HIGH TEMP") and to the minimal allowed water temperature ("LOW TEMP"). In case in step 414 the water temperature is found to be above the HIGH TEMP limit, a cooling sequence 418 is initiated, and in the case the water is found in step 416 to be too cold, the heating sequence 420 is initiated.

At the next decision step 422, a mode is selected based on the user's input, between cooling only mode, heating only mode or automatic mode, designated 424, 426 and 428, respectively.

In the first decision step 430 of the heating mode, the body core temperature ("CORE TEMP") is compared to the desired body core temperate ("SET POINT"). Where the body core temperature is found to be above the set point, the system is primed to enter to a standby mode 432, namely the heating function is terminated. During the standby mode, the core temperature is continuously measured and compared to the set point.

When the core temperature is determined to be below the set point, the water temperature is compared to the high temperature at 434 and if the water temperature is below the high temp, the heat mode 420 is initiated. If the water temperature is found to be above high temp, the system is primed again to enter into a standby mode 432.

In the first decision making step 440 of the cooling mode 424, the body core temperature is compared to the set point and if found to be belong the set point, the system is primed into standby mode 432. If the core temperature is below the set point, the system determines whether vasoconstriction of the skin has occurred 442. If there is no vasoconstriction, the cooling mode progresses into a next decision making step 444 where the water temperature is compared to the minimal allowed temperature. If water temperature is less than LOW TEMP then the system is primed to enter into a standby mode 432, and if above, the cooling sequence 418 is initiated.

In step 442, if vasoconstriction is found to have occurred (i.e. low heat conductance between the core and the periphery) notwithstanding the fact that there is a cooling mode, a heating sequence is initiated. When vasoconstriction is determined to have ceased, the cooling sequence is reinstated.

In a first decision making step 450, of the automatic mode 428, the core temperature is compared to the set point, if found to be below the set point, the system enters the heating mode 426. If the core temperature is found to be below the set point, the sequence proceeds to the next decision making step 452 and there, if the core temperature is found to be above the set point, the cooling sequence 424 is initiated. If the core temperature is found to be below the set point, the system is shifted towards the standby mode.

In the algorithm described above, the only parameter controlled is the water temperature. It should be appreciated, that in other embodiments, parameters such as flow rate of the heat transfer fluid may also be controlled. In addition, various other parameters, such as blood temperature, based on data imported from artificial heart-lung apparatus, may also be factored in the system's output.

As will be appreciated, the determination of the occurrence of vasoconstriction may be based on a variety of parameters, as noted above in the description, making use of data received from one or more of the above described sensing devices.

EXAMPLE 1

Experimental Procedure

Patients undergoing open heart surgery were divided randomly into two groups:-control group (20 patients) treated according to a routine thermal care method and an experimental group (40 patients) treated by the method of the invention consisting of a special garment which is fitted over the appropriate body parts of the patient prior to surgery. The temperature of the garment, which was adjustable, was set for the following temperature set points (the set point is a core body temperature set point, influenced by means of heating or cooling of the periphery, in accordance with the method of the invention):

1. In the induction room and until point of cardiopulmonary bypass the body temperature was set to 37° C.;
2. During the initial cardiopulmonary bypass phase, temperature was only recorded and towards the end of this phase when the blood was heated, at the same time the set point was made to be 37° C., thus simultaneously heating the periphery;
3. At the time of disconnection from the cardiopulmonary bypass and until transfer to recovery room the temperature was set to 37° C.
4. In the recovery room, during post-operative recovery (4 hours) the temperature was set to 37° C.

During the above steps, the skin temperature and core body temperature (rectal temperature) were recorded. Further, cardiac index and the systemic vascular resistance (measured by a Swan-Ganz catheter) were assessed at the following times: at induction of anesthesia, prior to initial incision, 30 minutes after incision, prior to cardiopulmonary bypass connection, at 5 and 30 minutes after cardiopulmonary bypass disconnection, at the end of the surgery and at one, two and four hours post-operatively.

Results

While the core body temperature of the treated subjects was maintained close to the 37° C. set point, within the range of about 36.5° C. and 37.5° C., the temperature of the control patients was, throughout all phases of the operation, about 1–2.5° C. lower.

The measured cardiac index of the patients treated is shown in the table that follows:

| Cardiac Index $L/min/m^2$ | | |
|---|---|---|
| Event | Allon | Control |
| Induction of anesthesia | 2.41 | 2.31 |
| Prior to incision | 2.46 | 2.06 |
| 30 minutes post-incision | 2.41 | 2.17 |
| 60 minutes post-incision | 2.69 | 2.27 |
| Prior to CPB | 2.61 | 2.28 |
| 5 minutes post-CPB | 3.52 | 2.62 |
| 30 minutes post-CPB | 3.47 | 2.57 |
| End of Surgery | 3.34 | 2.6 |
| 1 hour post-op | 3.07 | 2.53 |
| 2 hours post-op | 3.2 | 2.52 |
| 4 hours post-op | 3.26 | 2.58 |

The measured systemic vascular resistance of the patients treated in accordance with the invention was as follows:

| Systemic Vascular Resistance $dynes\text{-}sec\text{-}cm^{-5}$ | | |
|---|---|---|
| Event | Allon | Control |
| Induction of anesthesia | 1285 | 1571 |
| Prior to incision | 1265 | 1588 |
| 30 minutes post-incision | 1287 | 1572 |
| 60 minutes post-incision | 1136 | 1331 |
| Prior to CPB | 1182 | 1499 |
| 5 minutes post-CPB | 900 | 1246 |
| 30 minutes post-CPB | 917 | 1440 |
| End of Surgery | 942 | 1305 |
| 1 hour post-op | 1099 | 1617 |
| 2 hours post-op | 1057 | 1571 |
| 4 hours post-op | 984 | 1256 |

The results show that the inventive procedure gave superior results over the prior art.

EXAMPLE 2

Cardiac Troponin I plasma levels during and following surgery when patients were subjected to body heat control in accordance with the invention, were compared to those of patients treated with the routine body temperature control methods: Warming, blankets, fluid warming, bearhugger, etc.

28 patients were tested. Of these 28 patients, 18 were subjected to heat control in accordance with the invention, while 10 were served as control. In all patients the level of cardiac Troponin I (cTn-I) in serum was measured. The level of cTn-I is an accurate diagnostic marker for detecting minor myocardial injury. The results are shown in FIG. 13.

As can be seen, there were statistically significant differences between the two groups: in the cTn-I levels measured at the end of the cardio-pulmonary bypass period (p=0.016), at the end of surgery (p=0.031) and post-operatively (p=0.013).

These results suggest that keeping normothermia using the system of the invention ( "ALLON") may decrease the potential damage to the myocardium during coronary artery bypass surgery.

The results in the examples above show the high efficacy of the method and system of the invention in improving cardiovascular parameters as compared to patients which underwent a similar procedure without body temperature control in accordance with the invention.

What is claimed is:

1. A method for improving cardiovascular parameters in a patient undergoing a medical procedure under general anesthesia, comprising:

(a) contacting a substantial portion of the patient's external body surface, without covering the areas where surgical procedures are performed with a heat exchanger which can transfer heat to or absorb heat from the body surface;

(b) continuously measuring parameters from the body including at least the actual body core temperature (aBCT) and determining a parameter indicative of the heat transfer dynamics (HTD) between the body's periphery and the body's core; and (c) in a processor, receiving data signals corresponding to the measured parameters and to the determined HTD, comparing the aBCT with a desired body core temperature (dBCT) needed in order to maintain desired cardiovascular parameters based on the aBCT/dBCT difference, and emitting a control signal to control heat transfer properties of said heat exchanger.

2. A method according to claim 1, wherein the heat transfer to and from the body portion is achieved by transfer of heat control fluid through said heat exchanger.

3. A method according to claim 1, comprising continuously monitoring temperature at a skin portion proximal to a skin portion in which the heat exchanger is applied, and determining said HTD based on the rate of temperature change at said skin portion.

4. A method according to claim 1, wherein said heat exchanger is in a form of a garment to be worn over a portion of the body.

5. A method according to claim 4, having adhesive patches or flaps at edges of the garment to permit fixing of the garment to the body of the patient.

6. A method according to claim 4, wherein said garment comprises at least two layers defining between them a fluid transfer space for transfer of heat control fluids therethrough.

* * * * *